(12) United States Patent
Caleffi

(10) Patent No.: US 7,264,607 B2
(45) Date of Patent: Sep. 4, 2007

(54) CIRCUIT FOR EXTRACORPOREAL BLOOD CIRCULATION

(75) Inventor: Luca Caleffi, Mirandola (IT)

(73) Assignee: Gambro Lundia AB, Lund (SE)

( * ) Notice: Subject to any disclaimer, the term of this patent is extended or adjusted under 35 U.S.C. 154(b) by 458 days.

(21) Appl. No.: 10/804,165

(22) Filed: Mar. 19, 2004

(65) Prior Publication Data

US 2004/0186416 A1     Sep. 23, 2004

Related U.S. Application Data

(60) Provisional application No. 60/480,408, filed on Jun. 23, 2003.

(30) Foreign Application Priority Data

Mar. 21, 2003   (IT) .......................... MO2003A0080

(51) Int. Cl.
  *A61M 37/00*  (2006.01)
  *A61M 5/00*   (2006.01)
(52) U.S. Cl. .................. 604/6.16; 604/4.01; 604/7; 604/6.01; 604/6.11; 604/6.15; 604/6.05
(58) Field of Classification Search ............... 604/6.16, 604/7, 6.01, 6.11, 6.15, 6.05
See application file for complete search history.

(56) References Cited

U.S. PATENT DOCUMENTS

| | | | |
|---|---|---|---|
| 4,676,467 A | 6/1987 | Palsulich | |
| 4,798,090 A | 1/1989 | Heath et al. | |
| 4,885,001 A | 12/1989 | Leppert | |
| 5,188,588 A | 2/1993 | Schoendorfer et al. | |
| 6,306,346 B1 * | 10/2001 | Lindsay | ........................ 422/45 |
| 2005/0245871 A1 * | 11/2005 | Delnevo et al. | ............ 604/126 |
| 2006/0058774 A1 * | 3/2006 | Delnevo et al. | ............ 604/500 |

FOREIGN PATENT DOCUMENTS

| | | |
|---|---|---|
| EP | 0 134 436 A | 3/1985 |
| EP | 0 568 265 A2 | 11/1993 |
| GB | 2 176 717 A | 1/1987 |
| IT | 1222122 | 7/1987 |
| WO | WO 00/18482 A | 4/2000 |

OTHER PUBLICATIONS

International Preliminary Report on Patentability for International Application No. PCT/IB2004/000750.

* cited by examiner

*Primary Examiner*—Tatyana Zalukaeva
*Assistant Examiner*—Ginger Chapman
(74) *Attorney, Agent, or Firm*—Finnegan, Henderson, Farabow, Garrett & Dunner, L.L.P.

(57) ABSTRACT

A circuit for extracorporeal blood circulation, which is used for a single-needle dialysis, comprises a blood withdrawal line (2) having an arterial pump portion (23), and a blood return line (4) having a venous pump portion (43). Pump portions are designed to be coupled with corresponding peristaltic pumps (6), (7). An arterial expansion chamber (25) is arranged on the withdrawal line downstream from said arterial pump portion. A venous expansion chamber (45) is arranged on the return line upstream from said venous pump portion. The two expansion chambers are firmly joined one to the other into an integrated structure (9), which is equipped inside with two ducts connecting the arterial expansion chamber with two fluid connections attached outside to the integrated structure. The circuit can be assembled and disassembled from a dialysis machine easily and rapidly.

21 Claims, 6 Drawing Sheets

CIRCUIT FOR EXTRACORPOREAL BLOOD CIRCULATION

CROSS REFERENCE TO RELATED APPLICATIONS

This application claims the priority of Italian Application No. MO2003 A 000080, filed Mar. 21, 2003, and claims the benefit of U.S. Provisional Application No. 60/480,408, filed Jun. 23, 2003.

BACKGROUND OF THE INVENTION

The present invention relates to a circuit for extracorporeal blood circulation. In particular, though not exclusively, the invention can be advantageously used in single-needle dialysis.

Single-needle dialysis consists in a sequence of brief identical operating cycles. Each operating cycle comprises two stages: an arterial stage and a venous stage. In the arterial stage blood is taken from the patient, through a vascular access, and introduced into the extracorporeal circuit. In the venous stage blood, which has been previously stored in the extracorporeal circuit during the arterial stage, is returned to the patient after being purified through the same vascular access. In single-needle dialysis blood is taken from and returned to the patient through only one access element (for instance a needle or a catheter).

An advantage of single-needle dialysis consists indeed in the possibility to use, when necessary, only one central access element, thus reducing vascular trauma and the risk of thrombotic lesions with respect to the use of two-way access elements or of two access elements coupled together.

Similarly, single-needle dialysis involves a reduced fistula trauma and a subsequent longer duration of said fistula.

Another advantage is for the patient the introduction of only one needle instead of two.

Generally, the extracorporeal circuit for single-needle dialysis comprises: a withdrawal line, which conveys blood from the vascular access to a dialyzing filter; a return line, which conveys blood from the dialyzing filter back to the vascular access; and one or more expansion chambers, arranged before and/or after the dialyzing filter, where blood is stored during the arterial stage. The only access element (needle or catheter) is connected to the withdrawal and return lines through a Y-connection.

At least one arterial pump operates on the withdrawal line. In many cases there is also a venous blood pump operating on the return line.

In the course of the following description we shall refer for reasons of clearness and shortness to extracorporeal blood circuits for single-needle dialysis, equipped with at least two expansion chambers (an arterial chamber and a venous chamber) and designed to operate with two pumps (an arterial pump and a venous pump).

Line closing devices (for instance shaped as pliers) act on the circuit and are arranged close to the ways of the Y-connection connected to the withdrawal and return lines. Said closing devices are automatically controlled at the beginning of the arterial stage, so as to open the withdrawal line and close the return line, and conversely at the beginning of the venous stage, so as to open the return line and close the withdrawal line.

The system controlling switching from one stage to another is usually a pressure/pressure system, in which during the arterial stage (or withdrawal stage) the arterial pump (upstream from the dialyzing filter) fills with blood the filter and the expansion chambers, whereas the venous pump (downstream from the filter) is off; when pressure reaches in a given point of the circuit a given value, the arterial pump stops and the venous pump automatically starts operating (beginning of venous stage or return stage) and conveys blood from the filter to the patient; when pressure in the aforesaid given point of the circuit sinks beyond a given lower limit, the venous pump stops and a new operating cycle begins. This switching procedure allows a relatively high haematic flow with respect to other switching systems.

During the arterial stage a given blood volume (corresponding to $V_c$=volume of blood treated for each cycle) is stored in the dialysis filter, in the venous expansion chamber and in the arterial expansion chamber. During this arterial stage blood pressure in the extracorporeal system rises. In the arterial stage blood filling the expansion chambers compresses the air contained in said chambers.

The volume of blood treated for each cycle, $V_c$, is together with the average haematic flow one of the parameters indicating the efficiency of a single-needle dialysis. Said volume $V_c$ is substantially proportional to air volumes within the venous and arterial expansion chambers at the end of the venous stage. In order to obtain sufficiently high values related to the volume of blood treated for each cycle, for instance of about at least 40-60 ml, it is therefore necessary to have two expansion chambers having quite a large size.

Said volume $V_c$ can therefore be considered as proportional to blood pressure difference, measured for instance on the venous line, between the end of the arterial stage and the end of the venous stage. In other words, $V_c$ is proportional to $p_2-p_1$ where $p_1$ is pressure in the venous expansion chamber at the end of the venous stage, and $p_2$ is pressure in the venous expansion chamber at the end of the arterial stage. Minimum pressure, $p_1$, is generally higher than zero.

In order to achieve high values of $V_c$ it is therefore possible, on a theoretical level, to build up a proper pressure gap $p_2-p_1$ between the arterial withdrawal stage and the venous return stage. However, said pressure gap $p_2-p_1$ is necessarily limited, generally to values between 100 and 200 mmHg, because too high a pressure gap could result in an undesired back-filtration, particularly in the case of reduced ultrafiltration or ultrafiltration with highly permeable filters.

Said volume $V_c$ is further proportional to the compliance of the dialysis filter. It should be observed, however, that commonly used filters have relatively low compliance values, above all capillary filters.

In short, the volume of blood treated pro cycle $V_c$, and therefore the efficiency of single-needle dialysis, depends first on the shape, the size and the efficiency of the expansion chambers.

It should be reminded that it is possible, on a theoretical level, to use only one expansion chamber. Note that the use of two expansion chambers instead of one affects the flow through the dialysis filter; if only the venous chamber is present, blood in the dialyzing filter stands still in the venous stage and flows in the arterial stage, so that flow is intermittent; in the same way, if only the arterial chamber is present, blood flows within the filter intermittently, since it stands still in the arterial stage and moves in the venous stage; conversely, using two expansion chambers flow is almost continuous, although normally variable switching from one stage to another one. Thanks to the continuity of the haematic flow, there are no blood staunching stages, thus reducing the danger of blood coagulation phenomena.

The use of two chambers is therefore advisable both in order to obtain a continuous haematic flow, thus avoiding blood staunching, and to obtain a high volume of blood treated for each cycle, even with low values of pressure gap and with low compliance filters.

The present invention refers to an extracorporeal circuit equipped with at least. two expansion chambers; at least an (arterial) chamber is located in a portion of the withdrawal line between the arterial blood pump and the blood treatment unit (dialyzing filter), and at least another (venous) chamber is located in the return line. In case of a circuit equipped also with a venous blood pump, the venous expansion chamber is located in a return line portion between the treatment unit and the venous pump.

It is generally preferable to use two expansion chambers having the same volume, or if different, with the venous chamber larger than the arterial chamber. The total volume of the two expansion chambers is generally not below at least 150 ml.

For a proper use of the expansion chambers, the latter should be almost completely empty of blood (about 5-10 ml of minimum filling pro chamber) at the end of each venous stage: as a matter of fact, the higher the air volume at the end of the venous stage, the higher the volume of blood treated pro cycle $V_c$.

The extracorporeal circuit for single-needle dialysis as known, carried out according to the precharacterizing portion of claim 1, is normally equipped with a double pump. The pump operating on the withdrawal line (arterial pump) is usually a roll peristaltic rotary pump. The withdrawal line comprises a pump portion designed to be coupled with the peristaltic pump; said pump portion generally consists of a flexible tube having a diameter, both inner and outer, larger than the diameter of conventional conveying tubes, which form the other flexible portions of the line that are not associated to the pump.

The pump portion is generally connected to the rest of the circuit by means of two fittings made of stiff plastic, one for each end of the pump portion, each of which comprises a stiff sleeve, with an inner diameter variation, having a first opening with a larger diameter, into which an end of the pump portion is introduced and glued, and a second opening opposite the first one having a smaller diameter, into which an end of a conventional extracorporeal circulation tube is introduced and glued.

Said structure makes the circuit complicated from the constructive point of view and increases its manufacturing costs; as a matter of fact, beyond positioning two connecting sleeves for a pump portion it is also necessary to carry out several operations involving the introduction and gluing of the tubes within said fittings.

In said known circuit the arterial and venous expansion chambers, one arranged after the arterial pump and the other one arranged before the venous pump, consist of two separate containers made of transparent plastic, each of which, generally having an axial symmetric shape, is equipped on its bottom with two cylindrical connections placed one beside the other, with vertical axis, an inlet and an outlet one. Each container is attached in a removable way, with a joint between two elastic arms, to a container-holder, which can also be attached in a removable way to an area arranged on one side of the dialysis machine.

During the stage of preparation of a single-needle dialysis treatment, the operator should carry out a series of manual operations aiming at connecting operatively the haematic module to the dialysis machine: said operations comprise among other things the assembly of the container-holder to the machine, the attachment with a joint of the expansion chambers to the container-holder, the fluid connection of the withdrawal line and of the return line to the treatment unit (dialyzing filter), the arrangement of the pump portion of the return line around the corresponding venous blood pump, and so on. Said preparatory operations involve relatively long times and a given difficulty for various reasons: firstly due to the fact that the container-holder should be attached to the machine; secondly, due to the low practicality and functionality of said container-holder; thirdly due to the arrangement of the circuit portions between the treatment unit and the expansion chambers, which makes the manual connection of said circuit portions to the expansion chambers quite difficult; eventually due to the difficulty of arranging the venous pump portion around the corresponding pump.

SUMMARY OF THE INVENTION

An aim of the present invention is to provide an extracorporeal circuit which can obviate the aforesaid limitations and drawbacks of the prior art.

Another aim of the present invention is to provide an extracorporeal circuit, which can be used in particular for an extracorporeal single-needle treatment and which is constructively simple and cheap.

A further aim of the invention is to carry out a disposable haematic module, equipped with at least two expansion chambers, an arterial chamber and a venous chamber, and to be attached simply and rapidly to an extracorporeal blood treatment machine.

An advantage of the invention is to make assembling and disassembling operations for the expansion chambers on the machine easier.

Another advantage of the present invention is to reduce the number of arranging and gluing operations for the ends of the tubes forming the blood lines into the corresponding tube supports.

These aims and advantages and others are all achieved by the present invention as characterized by one or more of the claims below.

According to a feature of the invention, the circuit for extracorporeal blood circulation comprises at least two expansion chambers, at least one of which is arranged on the withdrawal line after the arterial blood pump, joined into a single integrated structure.

Said structure can be easily introduced into and taken out of a proper seat arranged on the machine.

According to a feature of the invention, the expansion chambers forming the integrated structure are the two chambers which in the extracorporeal circuit are closer to the blood treatment unit, one on the withdrawal side and the other on the return side.

This allows to make the pathway followed by the flexible tubes connecting the expansion chambers with the blood treatment unit more rational.

According to a feature of the invention, the integrated structure is equipped outside with an outlet connection of the arterial expansion chamber, and an inlet connection of the venous chamber, i.e. the two connections which are fluidly closer to the treatment unit, both arranged on the same lateral side of the integrated structure, with reference to a practical embodiment.

This enables to reduce the length and meandering of the pathway followed by the tubes linking the treatment unit with the aforesaid connections of the expansion chambers. This feature further reduces the risk of kinking of said tubes, in other words the occlusion due to an excessive folding of the flexible tubes.

According to a feature of the invention, said integrated structure is equipped inside with at least a first duct, which connects an expansion chamber with a connection attached outside to the integrated structure, said first duct having at least a length of its pathway that goes through a central portion of the integrated structure dividing the two expansion chambers.

This enables a more rational arrangement, outside the integrated structure, of the connectors for the flexible tubes of the circuit. Furthermore, a part of the pathway followed by blood takes place in a stiff duct, and not flexible, which has constructive advantages beyond resulting in a higher compactness and an improved handling of the haematic module, as well as in an elimination of the risks of kinking of flexible tubes.

According to a feature of the invention, the aforesaid first duct has at least a length of its pathway going through an area of the integrated structure arranged above the expansion chamber and not in fluid connection to said first duct.

This enables to minimize the overall size of the integrated structure.

According to a feature of the invention, said integrated structure is equipped inside with at least two ducts, which put into fluid connection an expansion chamber with two corresponding fluid connections, an inlet and an outlet one, attached outside to the integrated structure.

This feature joins the advantages of the two features above.

According to a feature of the invention, at least an expansion chamber is provided with at least an inlet opening and an outlet opening, arranged in a lower portion of said chamber, the inlet opening being placed. slightly above the outlet opening.

This enables an efficient filling and washing of the circuit in the stage preceding the actual treatment (rinsing stage) without completely filling up the expansion chambers.

According to a feature of the invention, at least an expansion chamber has at least an inlet opening and an outlet opening, arranged close to an upper end and to a lower end, respectively, of an inclined bottom of said chamber.

This feature reduces the time required to carry out the preliminary filling and washing stage of the circuit.

According to a feature of the invention, the integrated structure has at least a deflecting element, shaped and arranged so as to deviate downwards the blood flow entering a lateral inlet of at least an expansion chamber.

This reduces the risk of an undesired foam formation within the expansion chamber.

According to a feature of the invention, said integrated structure has at least a pair of pump portion connections, which are connected to the two opposite ends of a pump portion of the return line, the latter being designed to be coupled with a rotary pump.

This reduces the number of operations involving the arrangement and gluing of tubes during circuit manufacturing.

According to a feature of the invention, the aforesaid pump portion extends on a vertical plane below said integrated structure.

This simplifies the installation of the integrated structure and of the pump portion on the machine.

According to a feature of the invention, said integrated structure is made of stiff material.

According to a feature of the invention, said integrated structure is used in an extracorporeal circuit for a single-needle dialysis treatment.

Further characteristics and advantages of the present invention will be more evident form the following detailed description of some embodiments of the invention, shown as a mere non-limiting example in the appended figures.

BRIEF DESCRIPTION OF THE DRAWINGS

Said description shall be made hereinafter with reference to the accompanying drawings, which are provided to a purely indicative and therefore non-limiting purpose, in which.

DETAILED DESCRIPTION

The numeral 1 globally refers to a haematic module for extracorporeal blood circulation. Said disposable haematic module is used in cooperation with an extracorporeal blood treatment machine, in particular a dialysis machine. When used coupled to the machine, said haematic module acts as extracorporeal blood circuit enabling a single-needle extracorporeal treatment, in particular a dialysis treatment. The arrows indicate the direction of blood during the circulation within the extracorporeal circuit.

Figure 7:
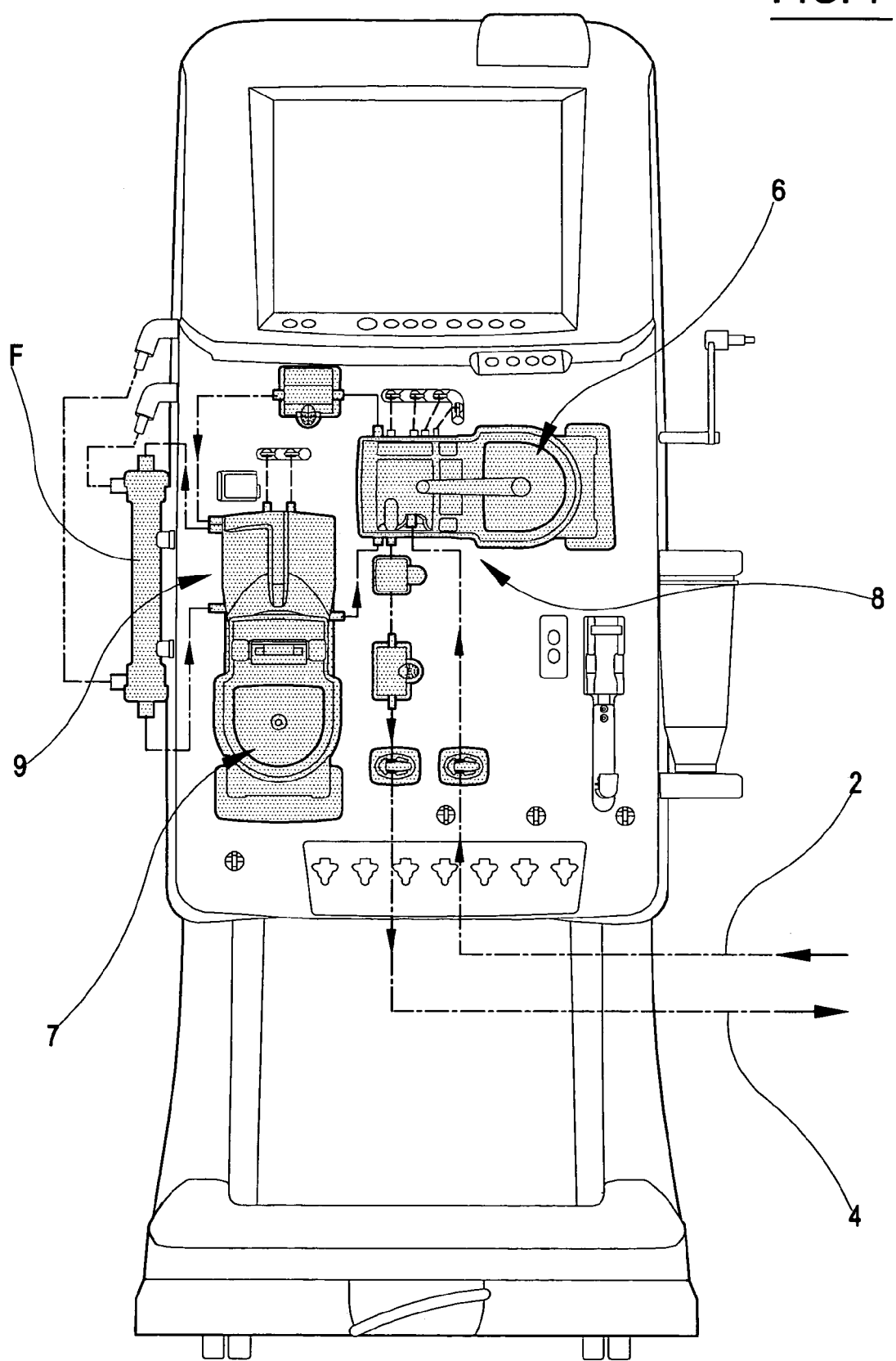
FIG. 7 shows the haematic module of FIG. 1 associated to a dialysis machine.

The machine, shown in FIG. 7, is designed in particular to carry out one or more of the following treatments: haemodialysis, haemofiltration, haemodiafiltration, pure ultrafiltration and other blood purification treatments, such as plasmapheresis and others.

The extracorporeal circuit comprises a blood withdrawal line 2 for taking blood from a patient, and a blood return line 4 for returning treated blood to the patient.

Said withdrawal line 2 has a first inlet end 21, designed to be put into communication with a patient's vascular access. The connection to the vascular access is carried out, as known, by means of a Y connection (not shown, having a first way connected to the withdrawal line, a second way connected to the return line, and a third way connected to a single vascular access element (for instance needle or catheter), introduced into the patient's cardiovascular system.

Said withdrawal line 2 has a second outlet end 22, designed to be connected to an inlet of a blood treatment unit, for instance a dialyzing filter F.

The withdrawal line 2 further comprises on an intermediate portion a bow-shaped pump portion 23 having a pre-determined axial length, designed to be coupled with a rotary pump, for circulating blood into the circuit. Said rotary withdrawal pump, also known as arterial pump, schematically shown in FIG. 1 and referred to with 6, is for instance a common roll peristaltic pump, with line occlusive rolls.

Said withdrawal line 2 also comprises an expansion chamber 24 (arterial expansion chamber) arranged on the line directly upwards from the pump portion 23.

The return line 4 has a first inlet end 41, designed to be connected to an outlet of the aforesaid treatment unit F. Both the second outlet end 22 of the withdrawal line and the first inlet end 41 of the return line are equipped each with a suitable connector for the connection to the treatment unit.

Said return line 4 has a second outlet end 42, designed to be put into communication with the patient's vascular access by means of the Y connection.

Said return line 4 further comprises on an intermediate line portion, a bow-shaped pump portion 43 having a pre-determined axial length, designed to be coupled with a rotary pump, for circulating blood into the circuit. Said rotary return pump, also known as venous pump, schematically shown in FIG. 1 and referred to with 7, is for instance a common roll peristaltic pump.

Said return line 4 comprises an expansion chamber 44 (venous expansion chamber) arranged on the line directly downwards from the pump portion 43.

The aforesaid arterial and venous expansion chambers, 24 and 44, which are fluidly separated one from the other, are integrated into one known box-shaped structure 8 with stiff walls.

The withdrawal line 2 is equipped with a further arterial expansion chamber 25 arranged on the withdrawal line between the intermediate pump portion 23 and the second outlet end 22. Said expansion chamber 25 is designed to contain a given blood storage volume.

A further venous expansion chamber 45 is arranged on the return line 4 upwards from the pump portion 43, so as to contain as well a given blood storage volume.

The expansion chambers 25 and 45 are those which in the extracorporeal circuit are fluidly closer to the blood treatment unit than the other expansion chambers 24 and 44.

The two further arterial and venous expansion chamber, 25 and 45, which are close to the treatment unit, are solidly joined one to the other. The two arterial and venous expansion chamber, 25 and 45, are stationary with respect to one and other. They are integral one to another. More in detail, they form an integrated structure 9 as one bloc with stiff walls. Said integrated structure 9 is made of a stiff and transparent plastic material.

The two arterial and venous expansion chambers, 25 and 45, which are firmed one to another so as to form a monobloc, are placed one beside the other on a central portion 90 extending mainly in vertical direction with reference to the practical embodiment of the expansion chambers.

Said central portion 90 between the two chambers 25 and 45, on which the two chambers are placed one beside the other, is also a dividing portion which fluidly separates said chambers and prevents a direct fluid communication between the expansion chambers 25 and 45.

Said integrated structure 9 has an arterial inlet connection 91 and an arterial outlet connection 92, in fluid connection with the arterial expansion chamber 25 placed downstream from the arterial pump 6. Furthermore, the integrated structure 9 has a venous inlet connection 93 and a venous outlet connection 94, in fluid connection with the venous expansion chamber 45 placed upwards from the venous pump 7.

The arterial inlet connection 91 is connected to a flexible portion of the withdrawal line 2, arranged downstream from the arterial pump portion 23.

The arterial outlet connection 92 is connected to a flexible portion of the withdrawal line 2 leading to the second outlet end 22.

The venous inlet connection 93 is connected to a flexible portion of the return line 4 leading to the first inlet end 41.

The venous outlet connection 94 is connected to a flexible portion of the return line 4 leading to the second outlet end 42. On said flexible portion of the return line 4 the venous expansion chamber 44 is arranged downstream from the venous pump portion 43.

The arterial outlet connection 92 and the venous inlet connection 93, both connected to line lengths communicating with the treatment unit, are arranged on the same side of the integrated structure 9.

Each connection 91, 92, 93, 94 comprises a stiff tubular element into which an end of a corresponding line length is axially inserted, said line length consisting of a flexible tube. Said end is firmly and permanently secured in a known way (generally by gluing) to the corresponding stiff connection on the integrated structure 9. Thanks to the tubular connections and to their joining system, the axis of each tubular connection defines an operating connection axis according to which the connection with the corresponding end of the blood conveying line is carried out.

The operating connection axes of the arterial outlet connection 92 and of the venous inlet connection 93 are parallel one to the other.

The arterial inlet connection 91 and the arterial outlet connection 92 are arranged one beside the other on the same side of the integrated structure 9. Said arterial connections, 91 and 92, are parallel one to the other.

The arterial inlet and outlet connections, 91 and 92 are far from the corresponding arterial expansion chamber 25, to which there are in fluid connection, and are attached to the monobloc integrated structure 9 on one side of the venous expansion chamber 45. Said side on which the arterial connections 91 and 92 fluidly closer to the treatment unit are placed, is a vertical lateral side of the venous expansion chamber 45, placed opposite the arterial expansion chamber 25.

The integrate structure 9 is equipped inside with an intake duct 95, which puts into fluid connection the arterial inlet connection 91 with the arterial expansion chamber 25. The intake duct 95 ends on one side into the arterial inlet connection 91 and on the other side into the arterial expansion chamber 25.

At least a part of the intake duct 95 passes through at least a part of the central portion 90 of the integrated structure 9, which is the dividing portion between the two expansion chambers 25 and 45.

The intake duct 95 comprises a first length 951 leading to the arterial inlet connection 91, placed above the underlying venous expansion chamber 45, with reference to a practical embodiment of the circuit.

The intake duct 95 comprises a second length 952 leading to the arterial expansion chamber, extending mainly in vertical direction with reference to a practical embodiment of the circuit, and arranged between the two expansion chambers 25 and 45 in the central portion 90 dividing one chamber from the other.

The first and second length 951 and 952 of the intake duct are connected one to the other by a short curved—about 90°—connection length.

The integrated structure 9 is equipped inside with a discharge duct 96, which puts into fluid connection the arterial outlet connection 92 with the arterial expansion chambers 25.

A part of the pathway followed by the discharge duct 96 is parallel to a part of the pathway followed by the intake duct 95.

The discharge duct 96 comprises a first length 961 leading to the arterial expansion chamber 25, placed below said chamber 25, where below refers to the operating form of the expansion chamber. Said first length 961 of the discharge duct follows a bow-shaped pathway with its concavity upwards.

The discharge duct 96 comprises a second length 962 extending mainly in vertical direction, and arranged in the central portion 90 dividing the two expansion chamber 25 and 45, beside the second vertical length 952 of the intake duct 95.

The discharge duct 96 comprises a third length 963 leading to the arterial outlet connection 92, extending mainly in a horizontal direction, placed above the venous expansion chamber 45, beside and below the first length 951 of the intake duct.

The longitudinal axes of the intake and discharge ducts, 95 and 96, parallel one to the other, are arranged on a lying plane corresponding to a median lying plane that is common to both venous and arterial expansion chambers 25 and 45. Said median lying plane common to both chambers 25 and 45 is also the lying plane with respect to which extends the whole integrated structure 9 integrating into one body the two aforesaid chambers. Also the stiff inlet and outlet, arterial and venous tubular connections, 91 and 92, 93 and 94, of the integrated structure 9 are arranged on said median lying plane.

The arterial expansion chamber 25 has an inlet opening 251 and an outlet opening 252, arranged in a lower portion of said chamber 25 on opposite sides of said chamber. The inlet opening 251 is located slightly above the outlet opening 252, where above refers to a practical embodiment of the circuit.

The arterial expansion chamber 25 has an inclined bottom extending between the inlet and outlet openings 251 and 252. Said openings 251 and 252 are arranged close to an upper end and to a lower end, respectively, of the inclined bottom of the chamber 25.

The venous expansion chamber 45 has an inlet opening 451 arranged laterally near the bottom of said chamber 45, and an outlet opening 452 arranged on a lower end of the bottom of the chamber 45.

The integrated structure 9 has a deflecting element 97, designed so as to deviate downwards the flow of blood at the lateral inlet opening 451 of the venous expansion chamber 45. The deflecting element 97 comprises a bow-shaped screen arranged opposite the lateral inlet opening 451, having an upper end secured to a lateral wall of the venous expansion chamber 45, and a free lower end. Said deflecting element is located above the outlet opening 452.

The integrated structure 9 has a pair of pump portion connections 98, which are connected to the two opposite ends of the pump portion 43 of the return line 4. Usually, the venous pump portion 43, being designed to be coupled with a rotary peristaltic pump, consists of a flexible tube with a given axial length, U-shaped, with features (for instance size) differing from other flexible tubes used in the blood circulation circuit. The pump portion connections 98 are tubular with greater inner and outer diameters than the connection 91, 92, 93 and 94. The venous pump portion 43 has the two opposite ends inserted and firmly joined into the connection 98.

The venous pump portion 43 extends on a substantially vertical plane, with reference to a practical embodiment of the circuit, arranged below the integrated structure. The venous pump portion 43 is substantially shaped as a U, with the concavity of said U pointing upwards.

The integrated structure 9 is provided inside with a first connection cavity 991, putting into fluid communication the two pump portion connections 98 with the venous expansion chamber 45.

The integrated structure 9 is further equipped inside with a second connection cavity 992, which puts into fluid communication the other pump portion connection 98 with the venous outlet connection 94 present on the integrated structure 9.

Figure 6:
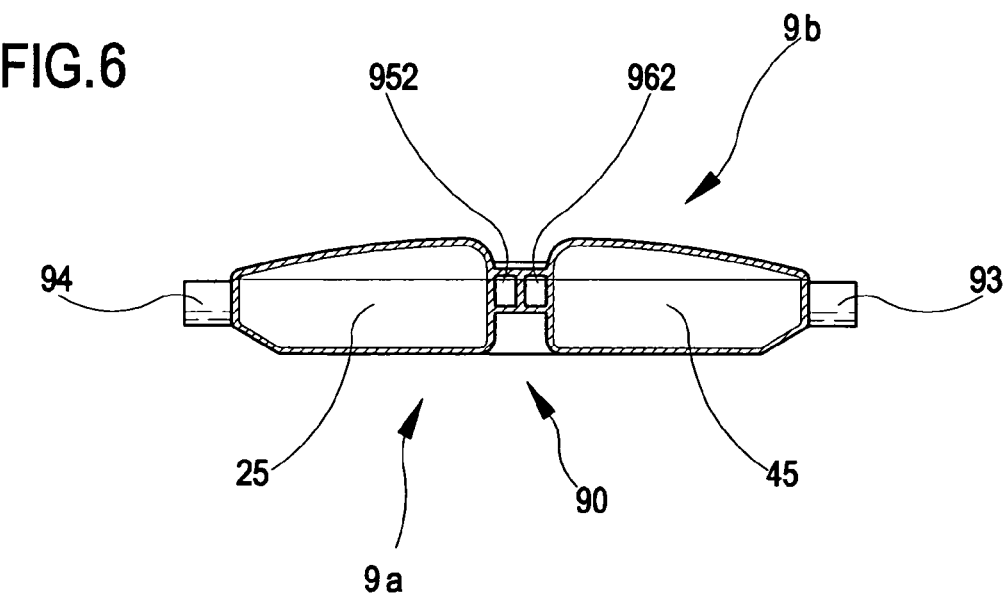
FIG. 6 shows the section VI-VI of FIG. 5.

The expansion chambers 25 and 45 forming the integrated structure 9 have each a substantially flattened shape and are definitely smaller than the other two (as is evident from the section in FIG. 6) and are placed one beside the other so that thanks to said arrangement the integrated structure is further flattened.

The integrated structure 9 comprises in one stiff bloc both the walls defining the expansion chambers 25 and 45 fluidly placed closer to the blood treatment unit, and the wall delimiting the intake and discharge ducts 95 and 96 leading to the arterial chamber 25, as well as the tubular connection 91, 92, 93, 94 and 98 to the various flexible blood circulation tubes, comprising the pump portion, and the deflecting element 97.

The integrated structure 9 has a stiff crosspiece 10 joining the two pump portion connections 98, in which a through opening 11 is obtained, which opening can act as fastening element for the integrated structure 9 to a support wall of the dialysis machine.

Figure 3:
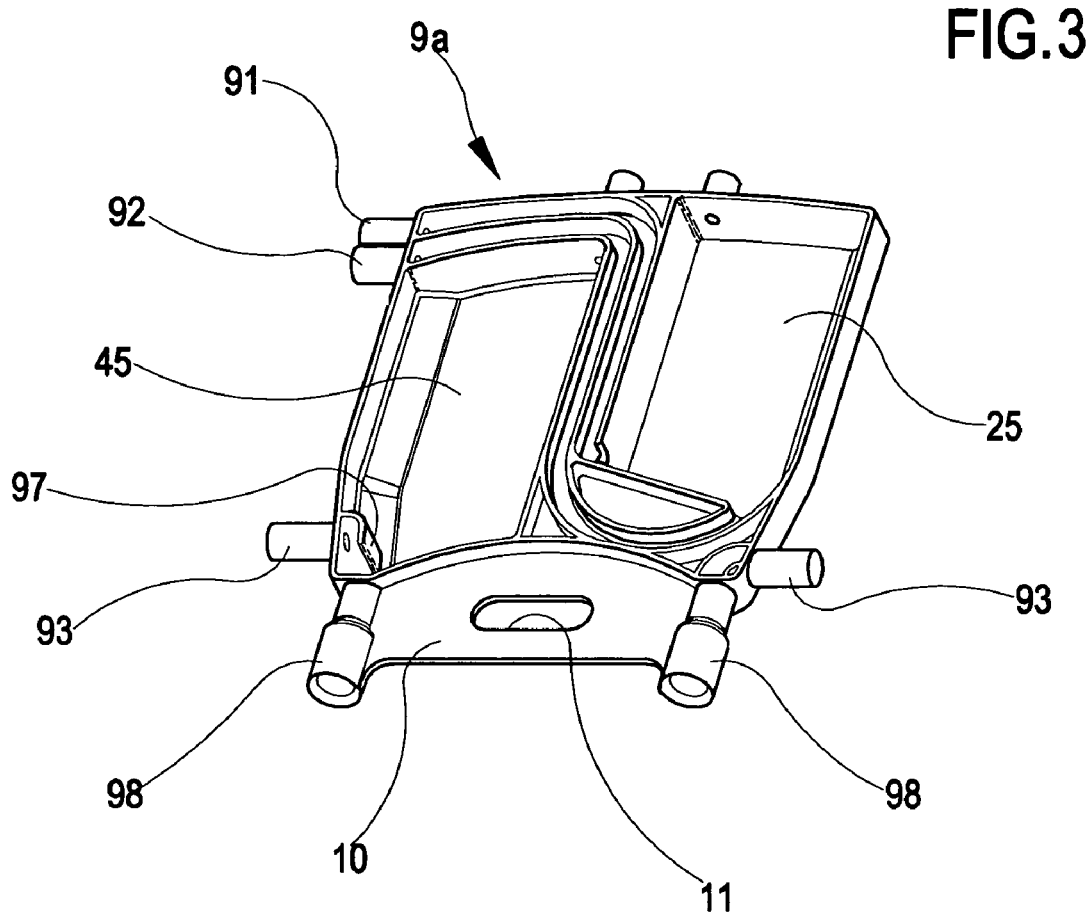
FIGS. 3 and 4 show two parts of the integrated structure before assembly.
Figure 4:
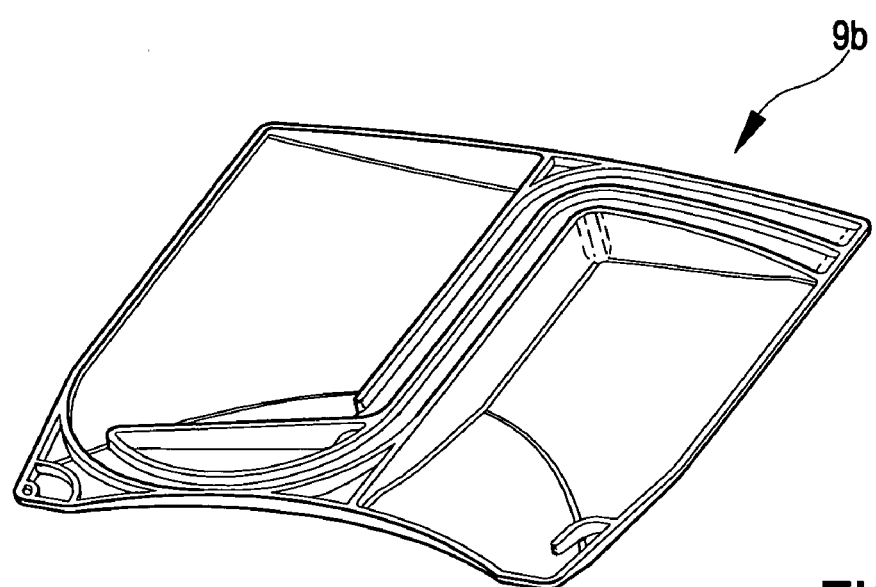
Figure 5:
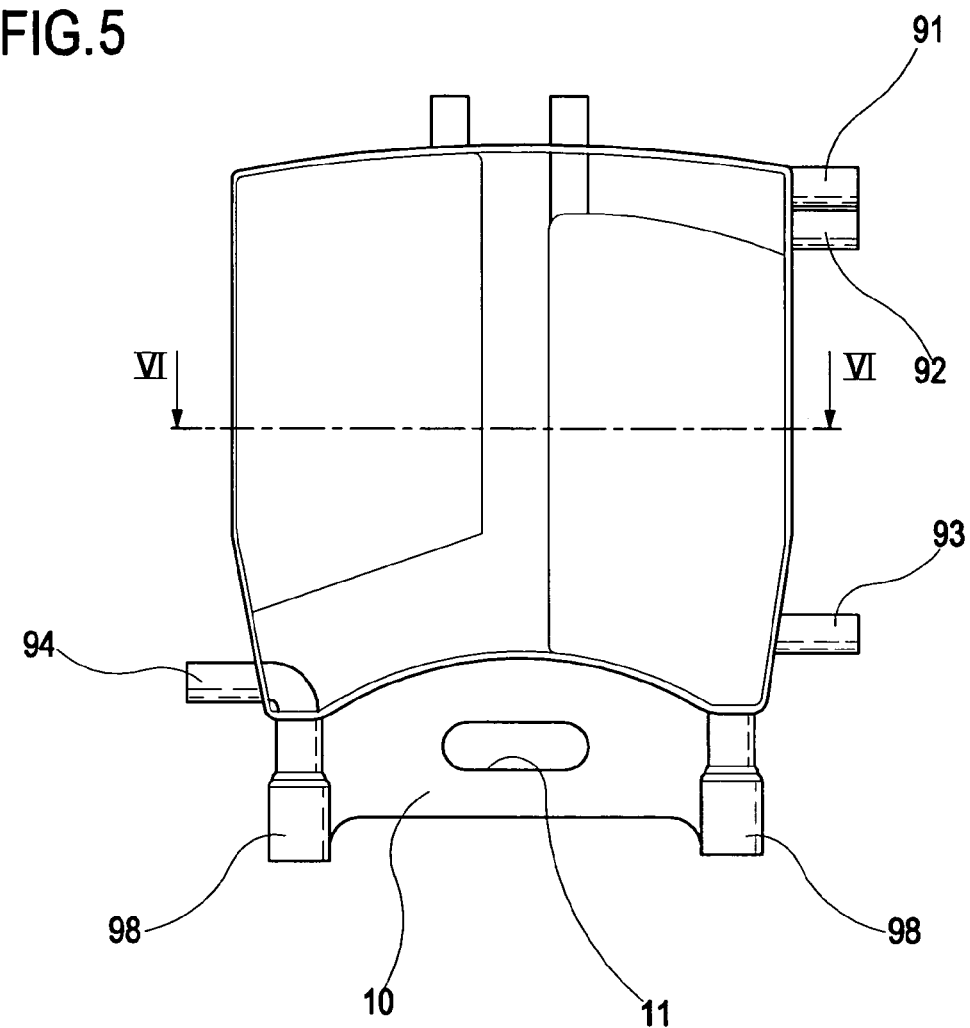
FIG. 5 shows a schematic front view of the integrated structure.

The integrated structure 9 is carried out by welding together two half-shells, a main body 9a (FIG. 3) and a cover 9b (FIG. 4), each being obtained by plastic injection molding. Welding takes place by heating and local softening in the joining areas of the plastic material, and subsequent joining of the joining areas and pressing of the two half-shells one against the other so long as to complete welding.

The dialysis machine comprises on its front face the arterial pump 6, the venous pump 7, a housing for the integrated structure 9, arranged above the venous pump 7, a revolving door for opening and closing said housing and for keeping the integrated structure in position during use, a seat for housing the box-shaped structure 8, arranged beside the arterial pump 6, a filter-holder for the dialyzing filter F.

Figure 1:
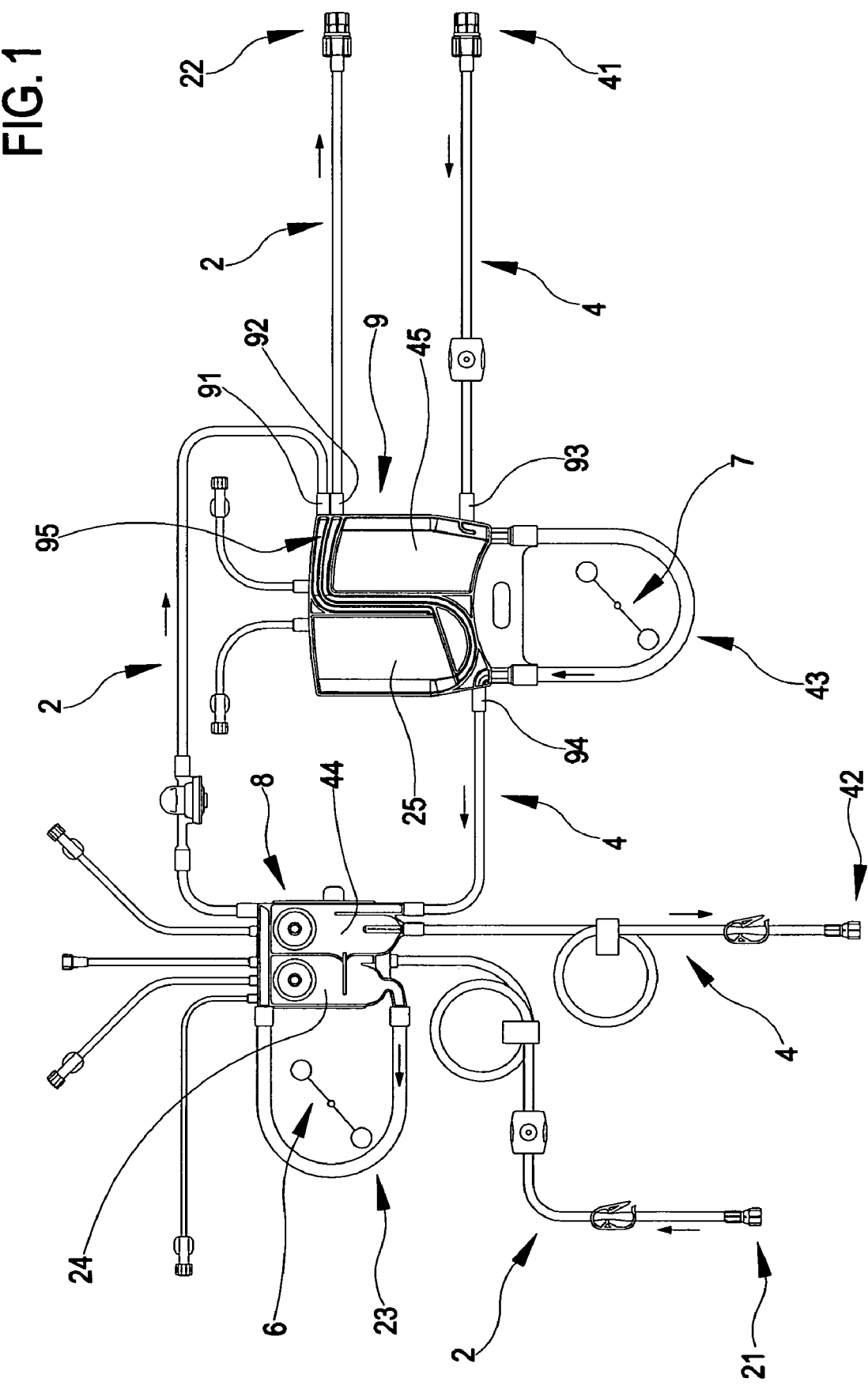
FIG. 1 shows a haematic module that can be operatively associated to an extracorporeal blood treatment machine, carried out according to the present invention.
Figure 2:
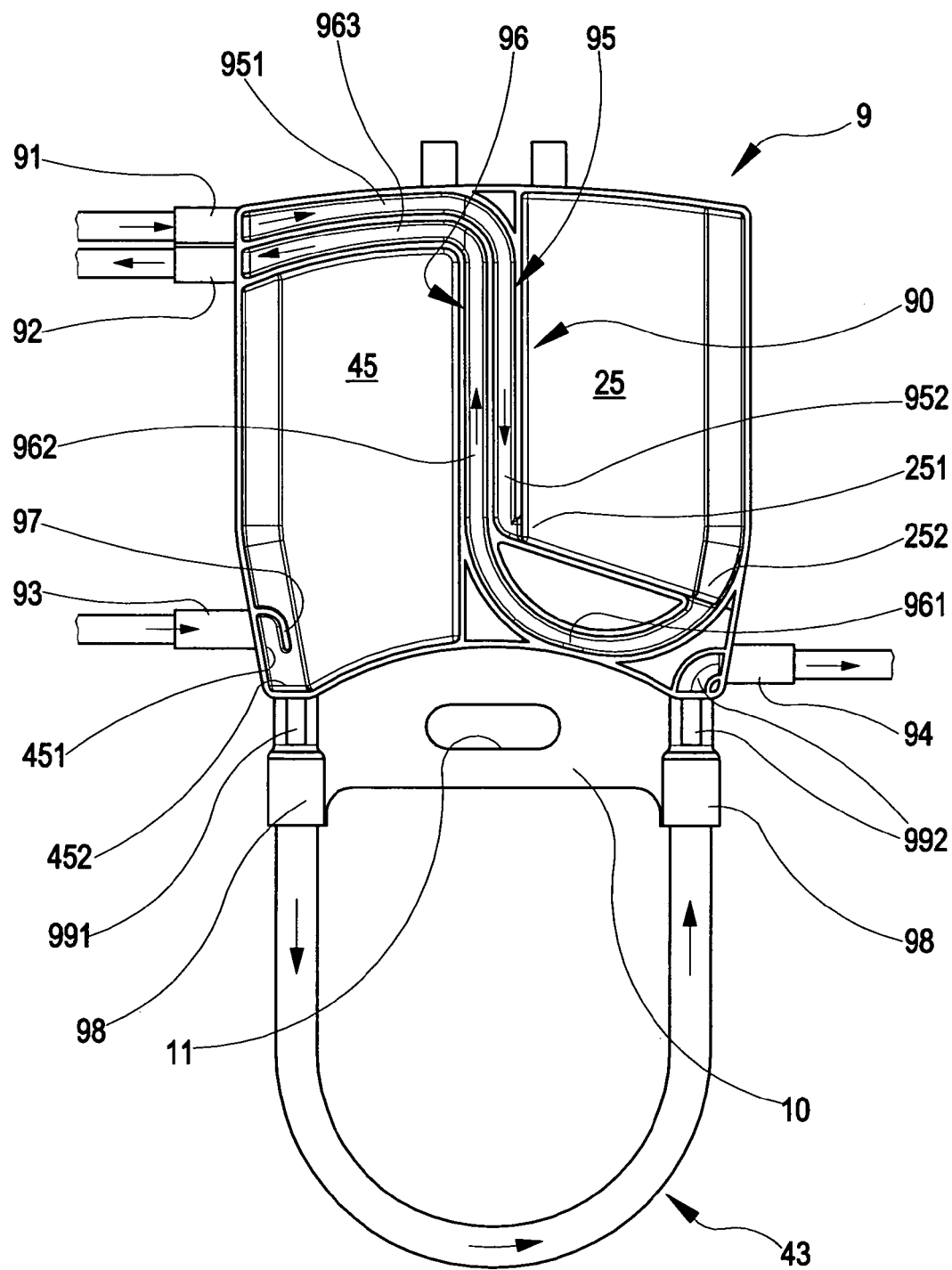
FIG. 2 shows an enlarged detail of FIG. 1 comprising the monobloc structure integrating two expansion chambers.
Figure 8:
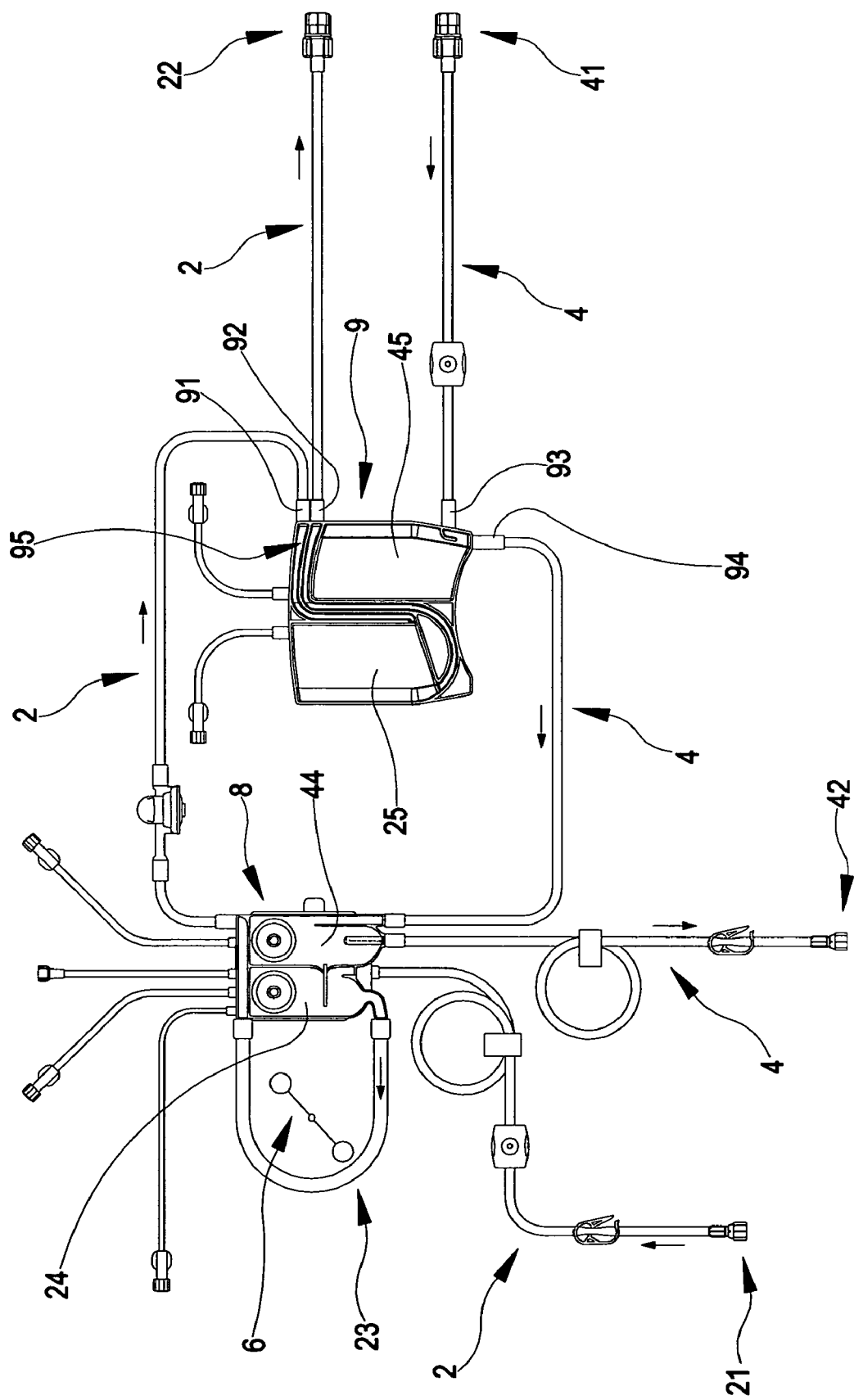
FIG. 8 shows a second embodiment of the haematic module according to the present invention.

FIG. 8 shows a second embodiment of the circuit, in which the main difference with respect to the circuit in FIG. 1 consists in the absence of the venous pump portion 43 and of its connections 98. The same elements in both circuits are referred to with the same numerals. The venous outlet connection 94, placed outside on the integrated structure, instead of being placed, as in FIG. 1, on the side of the arterial expansion chamber 25 opposite the side with the other connections 91, 92 and 93, in the circuit in FIG. 8 is arranged on the lower side of the integrated structure 9, close to the corner joining the bottom of the structure with the side with the other connections 91, 92 and 93, in direct communication with the outlet opening 452 of the venous expansion chamber 45.

The invention can undergo several practical changes involving constructive details, without leaving the protection a area of the inventive idea as claimed below.

The invention claimed is:

1. A circuit for extracorporeal blood circulation comprising:
- a blood withdrawal line for taking blood from a patient, having:
  - at least a first inlet end destined to be put into communication with a patient's vascular access,
  - at least a second outlet end configured to be connected with an inlet of a blood treatment unit, and
  - at least one pump portion configured to be coupled with a pump for blood circulation in the circuit;
- a blood return line for returning treated blood to the patient, having:
  - at least a first inlet end configured to be put into communication with an outlet of said treatment unit, and
  - at least a second outlet end configured to be connected with a patient's vascular access;
- at least one arterial chamber arranged on the blood withdrawal line between said pump portion and said second outlet end of the withdrawal line, and configured to contain a first blood storage volume;
- at least one venous chamber arranged on the blood return line and configured to contain a second blood storage volume,
- said at least one arterial chamber and said at least one venous chamber being solidly joined one to the other into an integrated structure including a stiff material, said integrated structure having an arterial inlet connection and an arterial outlet connection in fluid connection with the arterial chamber, and a venous inlet connection and a venous outlet connection in fluid connection with the venous chamber, said integrated structure being equipped inside with at least a first duct connecting a first of said arterial inlet connection, arterial outlet connection, venous inlet connection, or venous outlet connections to a first of said arterial and venous chambers,
- at least a part of said first duct passing through at least a part of a central portion of the integrated structure in which the arterial and venous chambers are placed one beside the other, said first duct having at least a length extending mainly in a vertical direction with reference to an operating configuration of the circuit, and arranged between the arterial and venous chambers,
- said integrated structure being further equipped inside with at least a second duct which puts into fluid connection a second of said arterial inlet connection, arterial outlet connection, venous inlet connection, or venous outlet connections with the first of said arterial and venous chambers, at least a part of a pathway followed by said second duct is parallel to at least a part of a pathway followed by said first duct,
- said integrated structure having at least a pair of pump portion connections connected to two opposite ends of a pump portion of the blood return line, said pair of pump portion connections being configured to be coupled with a pump, said integrated structure being further equipped inside with a first connection cavity, putting into fluid communication at least one of said pair of pump portion connections with the venous chamber, and a second connection cavity, putting into fluid communication at least one of said pump portion connections with the venous outlet connection attached to the integrated structure; and,
- a second venous chamber arranged on said blood return line downstream from said first of said arterial and venous chambers;
- a second arterial chamber arranged on said blood withdrawal line upstream from the pump portion on the withdrawal line;
- said second arterial and venous chambers being solidly joined with one another to form a box-shaped structure, said box-shaped structure being separate from said integrated structure.

2. A circuit according to claim 1, wherein said arterial outlet connection and said venous inlet connection are arranged on the same side of the integrated structure.

3. A circuit according to claim 1, wherein said arterial outlet connection and said venous inlet connection have an operating axis connecting to a corresponding portion of a blood conveying line, said operating connection axes of said arterial outlet and venous inlet connections being parallel to each other.

4. A circuit according to claim 1, wherein said arterial inlet connection and said arterial outlet connection are arranged one beside the other on the same side of the integrated structure.

5. A circuit according to claim 1, wherein said first of said arterial inlet connection, arterial outlet connection, venous inlet connection, and venous outlet connections is far from said first of said arterial and venous chambers and is placed on one side of a second of said arterial and venous chambers placed beside the first of said arterial and venous chambers.

6. A circuit according to claim 5, wherein the first of said arterial and venous chambers is placed opposite a side of the second of said arterial and venous chambers on which said first of said arterial inlet connection, arterial outlet connection, venous inlet connection, or venous outlet connections is located.

7. A circuit according to claim 1, wherein said first duct comprises at least a length leading to said first of said arterial inlet connection, arterial outlet connection, venous inlet connection, or venous outlet connections, arranged above a second of said arterial and venous chambers with reference to an operating configuration of the circuit.

8. A circuit according to claim 1, wherein said first of said arterial and venous chambers is the arterial chamber.

9. A circuit according to claim 1, wherein said second duct comprises at least a length leading to said first of said arterial and venous chambers and extending in a portion placed below the first of said arterial and venous chambers, with reference to an operating configuration of the circuit.

10. A circuit according to claim 9, wherein said length of the second duct follows a bow-shaped pathway having a concavity pointing upwards.

11. A circuit according to claim 1, wherein at least one of said arterial and venous chambers has at least an inlet opening and an outlet opening arranged in a lower portion of said at least one of said arterial and venous chambers, the inlet opening being located slightly above the outlet opening with reference to an operating configuration of the circuit.

12. A circuit according to claim 11, wherein said at least one of said arterial and venous chambers has an inclined bottom, said inlet opening and said outlet opening being placed close to an upper end and to a lower end, respectively, of said inclined bottom.

13. A circuit according to claim 1, wherein said integrated structure has at least one deflecting element, said deflecting element being configured to deviate downwards a blood flow entering a lateral inlet of at least one of said arterial and venous chambers.

14. A circuit according to claim 13, wherein said at least one deflecting element comprises a bow-shaped screen arranged before said lateral inlet, said screen having an upper end secured to a lateral wall of one of said arterial and venous chambers, and a free lower end.

15. A circuit according to claim 1, wherein said pump portion of the return line is arranged within the extracorporeal circuit downstream from a the venous chamber.

16. A circuit according to claim 1, wherein said pump portion extends on a substantially vertical plane, with reference to an operating configuration of the circuit, and is arranged below the integrated structure.

17. A circuit according to claim 1, wherein said arterial and venous chambers each have a substantially flattened shape and are joined one beside the other on one lateral side into the integrated structure.

18. A circuit according to claim 1, wherein said blood withdrawal line and said blood return line are designed to be connected with a single-needle vascular access.

19. A disposable haematic module designed to be used on an extracorporeal blood treatment machine, comprising an extracorporeal circuit according to claim 1.

20. A blood treatment machine designed to receive a haematic module according to claim 19.

21. A machine according to claim 20, configured to carry out one or more of the treatments selected from the group including; haemodialysis, haemofiltration, haemodiafiltration, and pure ultrafiltration.

* * * * *

UNITED STATES PATENT AND TRADEMARK OFFICE
CERTIFICATE OF CORRECTION

PATENT NO. : 7,264,607 B2  
APPLICATION NO. : 10/804165  
DATED : September 4, 2007  
INVENTOR(S) : Luca Caleffi Page 1 of 1

It is certified that error appears in the above-identified patent and that said Letters Patent is hereby corrected as shown below:

In claim 15, column 13, line 8, "from a the" should read --from the--.

In claim 21, column 14, line 12, "including;" should read --including:--.

Signed and Sealed this

Sixth Day of November, 2007

JON W. DUDAS  
*Director of the United States Patent and Trademark Office*